(12) United States Patent
Kumar et al.

(10) Patent No.: US 12,305,172 B2
(45) Date of Patent: May 20, 2025

(54) G-RICH ISO-RNA OLIGOMERS AS APTAMERS

(71) Applicant: COUNCIL OF SCIENTIFIC AND INDUSTRIAL RESEARCH AN INDIAN REGISTERED BODY INCORPORATED UNDER THE REGN. OF SOC. ACT (ACT XXI OF 1860), New Delhi (IN)

(72) Inventors: Vaijayanti Anil Kumar, Maharashtra (IN); Moneesha Fernandes, Maharashtra (IN); Atish Arun Wagh, Maharashtra (IN)

(73) Assignee: COUNCIL OF SCIENTIFIC AND INDUSTRIAL RESEARCH AN INDIAN REGISTERED RESEARCH AN INDIAN REGISTERED BODY INCORPORATED UNDER THE REGN. OF SOC. ACT (ACT XXI OF 1860), New Delhi (IN)

( * ) Notice: Subject to any disclaimer, the term of this patent is extended or adjusted under 35 U.S.C. 154(b) by 0 days.

(21) Appl. No.: 18/069,491

(22) Filed: Dec. 21, 2022

(65) Prior Publication Data

US 2023/0212586 A1     Jul. 6, 2023

(30) Foreign Application Priority Data

Dec. 25, 2021 (IN) .............................. 202113061089

(51) Int. Cl.
    *C12N 15/115*     (2010.01)
    *A61P 7/02*     (2006.01)

(52) U.S. Cl.
    CPC .............. *C12N 15/115* (2013.01); *A61P 7/02* (2018.01); *C12N 2310/16* (2013.01); *C12N 2310/314* (2013.01)

(58) Field of Classification Search
    CPC .................. C12N 15/115; A61P 7/02
    See application file for complete search history.

(56) References Cited

U.S. PATENT DOCUMENTS 9,914,928 B2     3/2018     Kumar et al.

FOREIGN PATENT DOCUMENTS

IN     324959     12/2014

OTHER PUBLICATIONS

Collie, Gavin W., "A crystallographic and modelling study of a human telomeric RNA (TERRA) quadruplex", Nucleic acids research 38.16, (2010), pp. 5569-5580.
Joachimi, Astrid, "A comparison of DNA and RNA quadruplex structures and stabilities", Bioorganic and medicinal chemistry 17.19, (2009), pp. 6811-6815.
Sacca, Barbara, "The effect of chemical modifications on the thermal stability of different G-quadruplex-forming oligonucleotides", Nucleic acids research 33.4, (2005), pp. 1182-1192.
Collie, Gavin W., et al., "A crystallographic and modelling study of a human telomeric RNA (TERRA) quadruplex", Nucleic Acids Research, 2010, vol. 38, No. 16; 5569-5580; doi:10.1093/nar/gkq259, (Apr. 22, 2010), 5569-5580.
Joachimi, Astrid, et al., "A comparison of DNA and RNA quadruplex structures and stabilities", Bioorganic & Medicinal Chemistry 17 (2009) 6811-6815, (Aug. 22, 2009), 6811-6815.
Sacca, Barbara, et al., "The effect of chemical modifications on the thermal stability of different G-quadruplex-forming oligonucleotides", Nucleic Acids Research, 2005, vol. 33, No. 4; doi:10.1093/nar/gki257, (2005), 1182-1192.

*Primary Examiner* — Richard A Schnizer
*Assistant Examiner* — Christina Tran
(74) *Attorney, Agent, or Firm* — Schwegman Lunberg & Woessner, P.A.

(57) ABSTRACT

The present invention relates to G-quadruplex forming iso-RNA oligomers and a process for the preparation thereof. The present invention further relates to a stable, guanine rich 2'-5'-linked iso-RNA selected from 2'-5'-linked iso-RNA. The instant 2'-5'-linked isoRNA oligomer of the thrombin binding aptamer (iso-rTBA) is highly resistant to RNase A and also resistant to other nucleases, including snake venom phosphodiesterase (SVPD) and forms a thermally stable functional G-quadruplex.

8 Claims, 11 Drawing Sheets

Figure 1A:
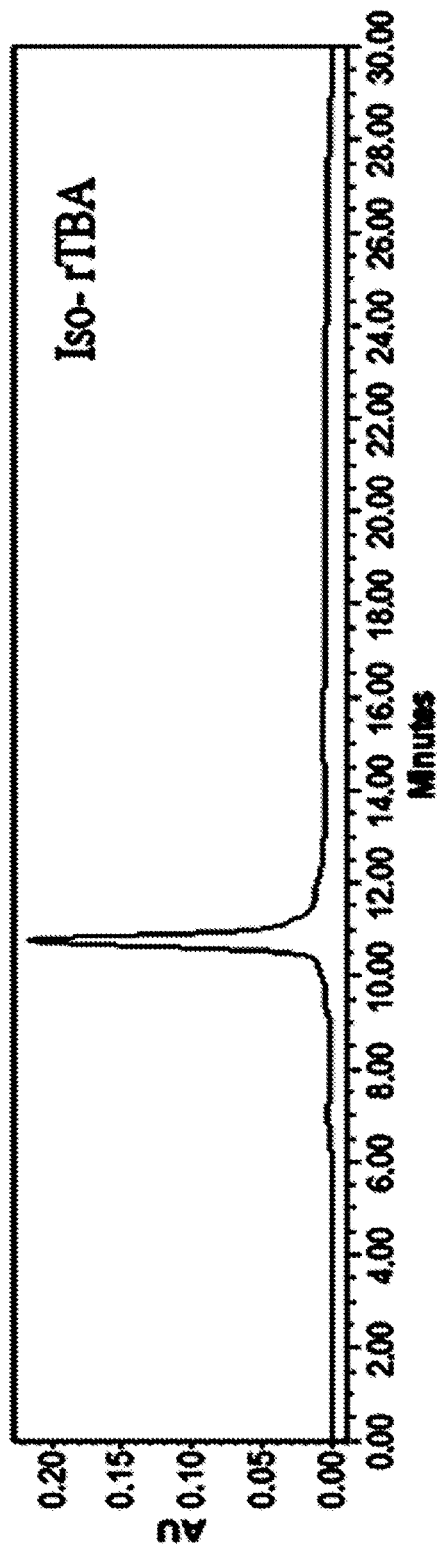

Specification includes a Sequence Listing.

```
SEQUENCE LISTING

Sequence total quantity: 1
SEQ ID NO: 1           moltype = RNA   length = 16
FEATURE                Location/Qualifiers
source                 1..16
                       mol_type = other RNA
                       organism = synthetic construct
SEQUENCE: 1
rggttggtgt ggttgg                                                    16
```

G-RICH ISO-RNA OLIGOMERS AS APTAMERS

CROSS-REFERENCES TO RELATED APPLICATIONS

The following complete specification is being filed as a patent of addition to the Indian patent No IN324959 [1561/DEL/2013] entitled "G-Quadruplex forming IsoDNA aptamers and a process for the preparation thereof" filed on May 24, 2013.

INCORPORATION BY REFERENCE OF SEQUENCE LISTING

A Sequence Listing is provided herewith as an xml file, "2959227US1.xml" created on Jan. 17, 2024 and having a size of 2,986 bytes. The content of the xml file is incorporated by reference herein in its entirety.

FIELD OF THE INVENTION

The present invention relates to stable, guanine-rich 2'-5' linked isoRNA oligomers capable of forming thermally stable unimolecular antiparallel G-quadruplexes and a process of preparation thereof. Additionally, the present invention includes isoRNA substitutions represented by 3'-R, where R includes, but is not limited to, OH, OMe, F, Cl, Br, OEt, OMOM, OMOE, etc. The present invention further relates to a composition comprising the guanine rich 2'-5' isoRNA sequences with one or more pharmaceutically acceptable excipients, wherein said composition exhibits anti-coagulant activity. The aptamers developed in the present invention have immense potential in the healthcare sector.

BACKGROUND OF THE INVENTION AND DESCRIPTION OF PRIOR ART

G-quadruplexes (G4s) are non-canonical secondary structures formed by G-rich nucleic acid sequences. The thrombin-binding DNA aptamer (TBA), 5'-d(GGTTGGTGTGGTTGG; SEQ ID NO: 2), a unimolecular antiparallel G-quadruplex, inhibited the thrombin-catalyzed polymerization of fibrinogen. It was shown that the G-quadruplex was critical for inhibitory activity as substitution of any of the guanines reduced the inhibition of thrombin.

Not all G-rich sequences have the propensity to form G-quadruplex structures, but G-rich sequences are essential for G-quadruplex formation. Metal ions and loop sequences connecting the guanosines also play critical roles in G-quadruplex formation.

Saccà B et al. demonstrated that RNA sequence can form G-quadruplex structure (rG4s). Given the chemical properties of RNAs, rG4s are generally more stable than dG4s of the same sequence (Saccà B., Lacroix L., Mergny J.-L., The effect of chemical modifications on the thermal stability of different G-quadruplex-forming oligonucleotides, Nucleic Acids Res. 2005; 33:1182-1192). G-quadruplexes are also indicated in non-coding RNAs (ncRNAs)-especially, long ncRNAs (lncRNA), telomeric repeat associated RNA (TERRA), the RNA component of the telomerase (TERC) and microRNAs—with yet mainly obscure biological significance (Collie G. W., Haider S. M., Neidle S., Parkinson G. N. A crystallographic and modelling study of a human telomeric RNA (TERRA) quadruplex; Nucleic Acids Res. 2010; 38:5569-5580). The additional 2'-OH group in the ribose ring populates a C3'-endo sugar pucker conformation, which significantly organizes the hydration shell and the hydrogen bond network and promotes a parallel G4 topology in rG4s (Collie G. W, Haider S. M., Neidle S., Parkinson G. N; A crystallographic and modelling study of a human telomeric RNA (TERRA) quadruplex; Nucleic Acids Res. 2010; 38:5569-5580).

In nature, unlike 2'-deoxyribose in DNA, RNA comprises a ribose sugar, but like DNA, it has phosphate links between carbons 3' and 5' of adjacent nucleosides, with a free 2'-hydroxy group. It is observed that 3'-5'-linked DNA carries genetic information, while 2'-5'-linked isoDNA and isoRNA are non-genetic. The 3'-5' linked RNA oligomers form multimolecular, parallel quadruplexes and 3'-5'-linked TBA RNA (Joachimi, A.; Benz, A.; Hartig, J. S. A comparison of DNA and RNA quadruplex structures and stabilities. Bioorg. Med. Chem. 2009, 17, 6811-6815) does not fold in a manner where it can elicit anti-coagulant activity. All the above reasons and the highly susceptible nature to RNases limit the scope of RNA in the field of aptamers.

The need for non-toxic and economically viable alternatives to traditional anticoagulants such as heparin has been recently being felt again in the SARS-COV-2 patient treatment and management context.

Jung et al (1994) disclose stable, guanine rich 2'-5' linked DNA sequences capable of forming duplexes, comprising an alternative four component genetic material.

U.S. Pat. No. 9,914,928 by the inventors, discloses a stable, non-genetic guanine rich 2'-5' linked isoDNA sequences capable of forming unimolecular antiparallel G quadruplexes, wherein the aptamers disclosed are based on DNA backbone. However, the present invention though reports the analogous sequence of RNA nucleobases, wherein T (thymine) nucleobase is replaced by U (uracil), but with an RNA backbone, i.e., it is a 2'-5'-linked ribose sugar in the backbone, because this oligomer has far better properties in comparison to the DNA TBA that is widely studied. The present aptamer is a good anti-coagulant, has much better nuclease stability, and is also thermally more stable. In addition, the monomers required for synthesis are readily available and at a much more reasonable price.

It may be noted that other G-rich RNA oligomers, including that of the TBA sequence, are known to form G-quadruplexes in the parallel topology. This implies multimolecular complexes that are unable to bind to thrombin or effect anticoagulation. Further, RNA oligomers, in general, are highly susceptible to RNases, the nucleases that degrade RNA. However, the developed iso-RNA (iso-rTBA) is not only stable to RNase A, and more stable than even the DNA TBA to snake venom phosphodiesterase, but it is also able to form thermally stabler unimolecular G-quadruplexes that fold in the antiparallel folding topology necessary for efficient binding to thrombin to ensure good anticoagulant activity.

Thus, in spite of the synthesis of 2'-5'-linked DNA sequences for biotechnological applications, there is still a need in the art to synthesize nuclease resistant 2'-5'-linked isoRNA sequences. This may be attributed to the relatively lower nuclease resistance of known TBA, or in general, DNA or to a larger extent, RNA oligomers.

Therefore, there is an unmet need in the art to provide an economically viable anticoagulant aptamer comprising iso-RNA (iso-rTBA) that binds to thrombin, which is stable to RNase A, and more stable than even the DNA-TBA to snake venom phosphodiesterase, while also forming thermally stable unimolecular G-quadruplexes that fold in the antiparallel folding topology necessary for efficient binding to thrombin to ensure good anticoagulant activity and is improved in efficacy, thermal stability and half-life (nuclease stability). This feature of the invention as anticoagulant is of great potential importance in the treatment of COVID-19 in addition to the treatment of other cardiovascular diseases.

OBJECTS OF THE INVENTION

The main objective of the present invention is therefore to provide stable, guanine-rich 2'-5' linked isoRNA sequences capable of forming thermally stable unimolecular antiparallel G-quadruplexes, that efficiently bind to thrombin, and exhibit a good anticoagulant activity.

Another object of the present invention is to provide stable, guanine-rich 2'-5'-linked isoRNA oligomers highly resistant to RNase and also resistant to other nucleases, such as snake venom phosphodiesterase (SVPD).

Yet another objective of the invention is to provide a 2'-5'-linked isoRNA with cost-effective RNA 2'-O-phosphoramidite monomers.

Still another objective of the invention is to provide isoRNA substitutions represented by 3'-R, wherein R includes but is not limited to OH, OMe, F, Cl, Br, OEt, OMOM, OMOE, and the like.

Yet another objective of the invention is to provide a process of preparation of G-quadruplex-forming isoRNA aptamers comprising stable, guanine-rich 2'-5'-linked isoRNA sequences.

Further objective of the invention is to provide a composition comprising the guanine-rich 2'-5'-linked isoRNA sequences with one or more pharmaceutically acceptable excipients.

SUMMARY OF THE INVENTION

Accordingly, in an aspect of the present invention, there is provided a stable, guanine-rich 2'-5'-linked isoRNA sequences capable of forming thermally stable unimolecular antiparallel G-quadruplexes for efficient binding to thrombin to ensure a good anticoagulant activity.

In an aspect of the present invention, the 2'-5'-linked isoRNA sequence forms unimolecular antiparallel G-quadruplexes.

In another aspect of the present invention, the 2'-5'-linked iso-RNA sequence includes an RNA 2'-O-phosphoramidite.

In still another aspect of the present invention, 2'-5' linked isoRNA includes RNA 2'-O-phosphoramidite monomers in comparison to the prohibitively expensive DNA 2'-O-phosphoramidite monomers of 2'-5'-linked isoDNA making its process of preparation cost effective.

In yet another aspect of the present invention, the 2'-5'-linked isoRNA (iso-rTBA) is an analogous sequence to the known thrombin-binding DNA aptamer (TBA) represented by SEQ ID No. 1.

In another aspect of the present invention, SEQ ID NO: 1 is represented by 5'-r(GGUUGGUGUGGUUGG)-2'.

In still another aspect of the present invention, the 'r' in the SEQ ID NO: 1 represents an RNA sequence and includes isoRNA substitutions represented by 3'-R, wherein R includes but is not limited to OH, OMe, F, Cl, Br, OEt, OMOM, OMOE, and the like.

In yet another aspect of the present invention, the 2'-5'-linked isoRNA sequence is highly resistant to RNase and also resistant to other nucleases, such as snake venom phosphodiesterase (SVPD).

In another aspect of the present invention, the 2'-5'-linked isoRNA oligomers are synthesized by β-cyanoethyl phosphoramidite chemistry using solid-phase synthesis.

In still another aspect of the present invention, the 2'-5'-linked RNA oligomer (iso-rTBA) is thermally stable and exhibits a melting temperature ($T_m$) of 52° C.

In yet another aspect of the present invention, the iso-rTBA: thrombin complex is found to be more thermally stable ($T_m$=29° C.) than the TBA: thrombin complex ($T_m$=22° C.) indicating the superiority of iso-rTBA.

In a further aspect, the present invention provides a composition comprising the guanine-rich 2'-5'-isoRNA sequences with one or more pharmaceutically acceptable excipients having anti-coagulant activity.

BRIEF DESCRIPTION OF THE ACCOMPANYING DRAWINGS

Figure 1B:
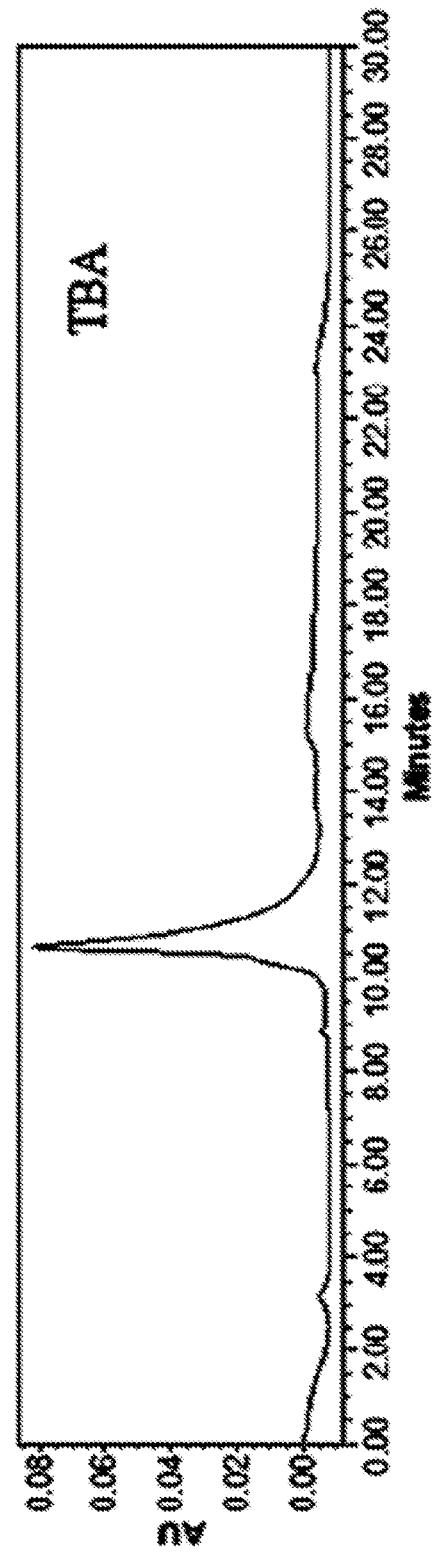

The invention has other advantages and features which will be more readily apparent from the following detailed description of the invention, when taken in conjunction with the accompanying drawings, in which:

FIG. 1: Depicts HPLC chromatograms of (A) Iso-rTBA, and (B) TBA, in accordance with an implementation of the present disclosure.

Figure 2A:
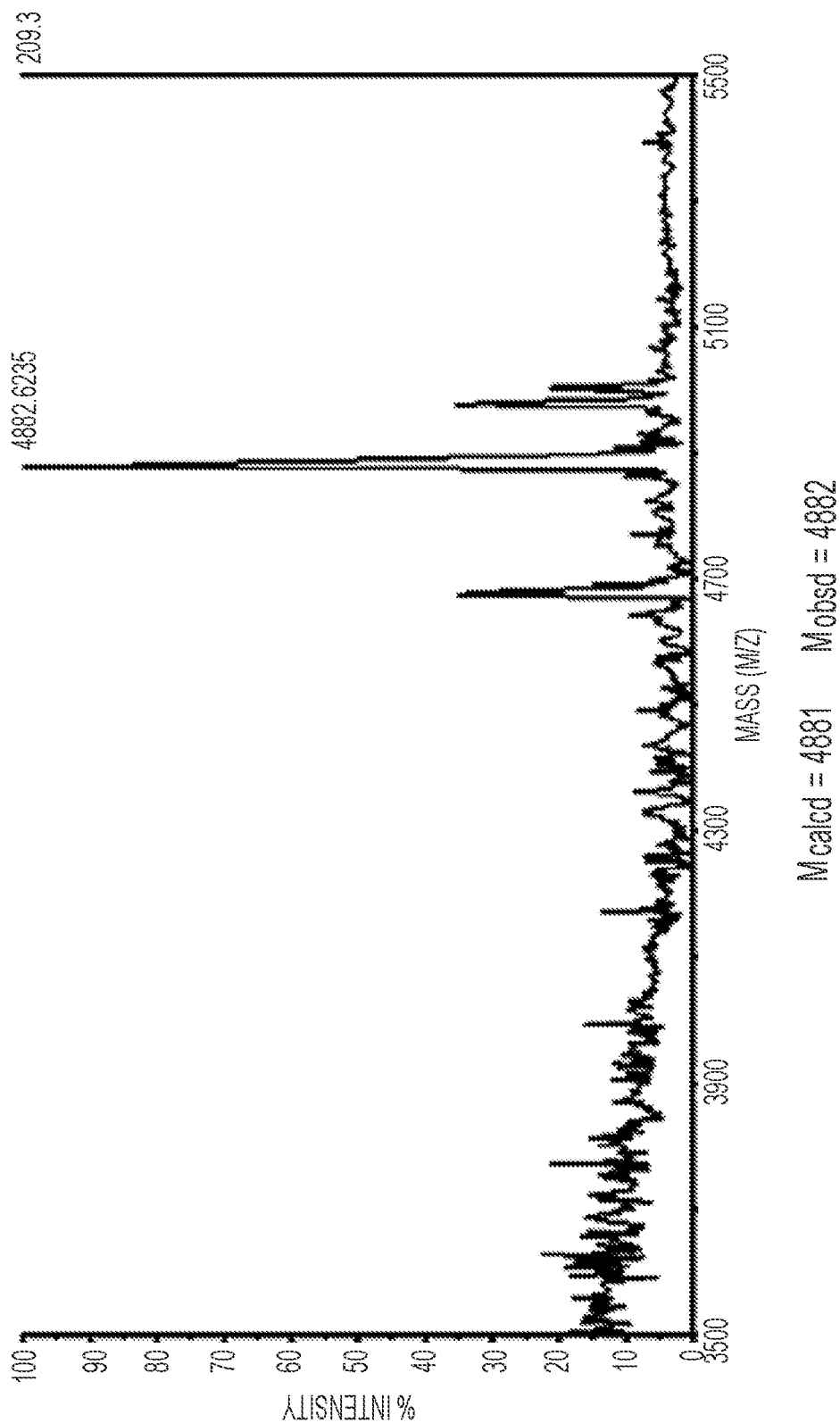
Figure 2B:
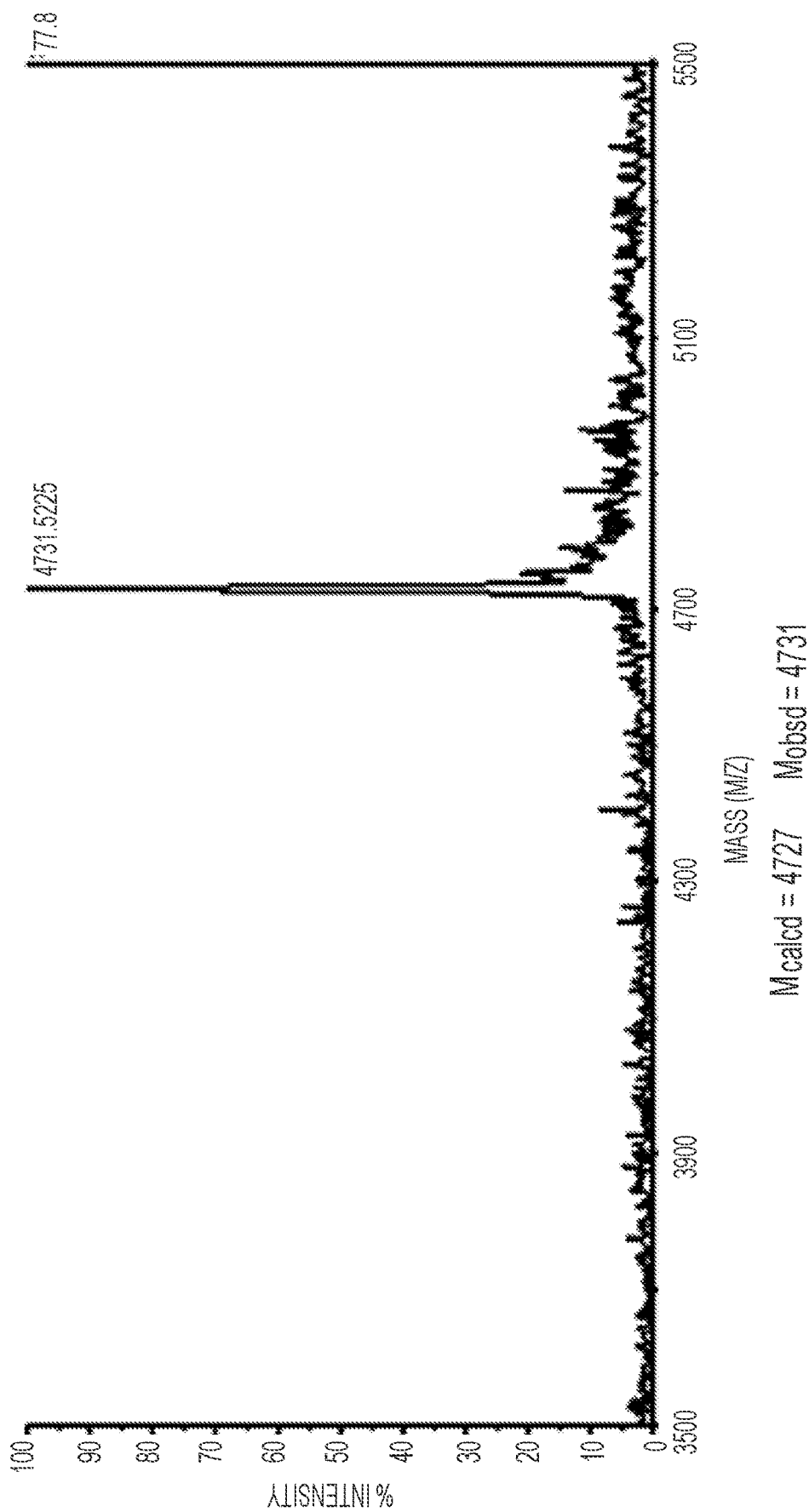

FIG. 2: Depicts MALDI-TOF mass spectra of (A) Iso-rTBA, and (B) TBA, in accordance with an implementation of the present disclosure.

Figure 3:
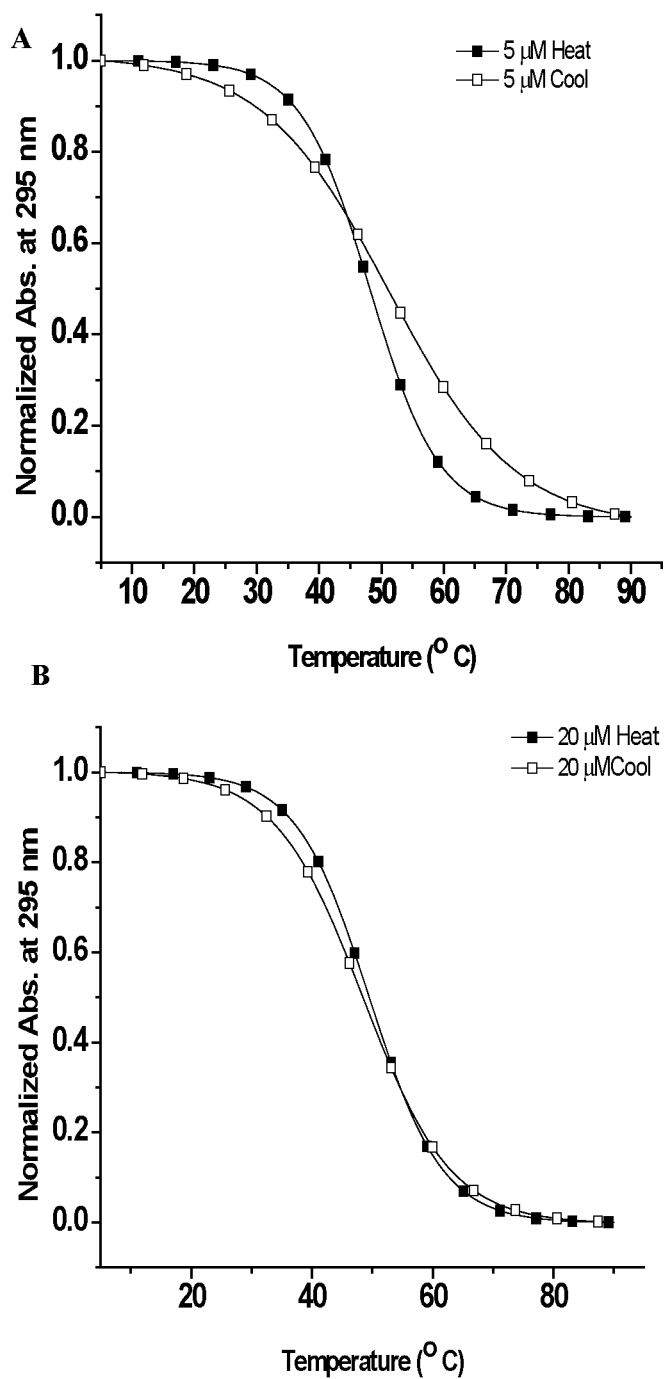

FIG. 3: Depicts normalized UV plots for heating and cooling cycles of iso-rTBA taken at 5 μM (A) and 20 μM (B) concentrations, monitored at 295 nm (Buffer: 10 mM potassium phosphate buffer, pH 7.2, containing 100 mM KCl), in accordance with an implementation of the present disclosure.

Figure 4:
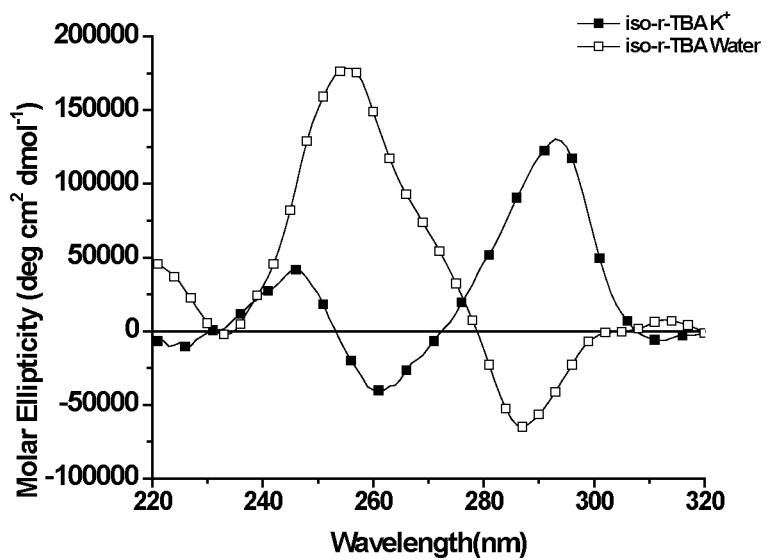

FIG. 4: Depicts CD spectrum of iso-rTBA in water (absence of added cations) and in 10 mM potassium phosphate buffer, pH 7.2, containing 100 mM KCl, in accordance with an implementation of the present disclosure.

Figure 5:
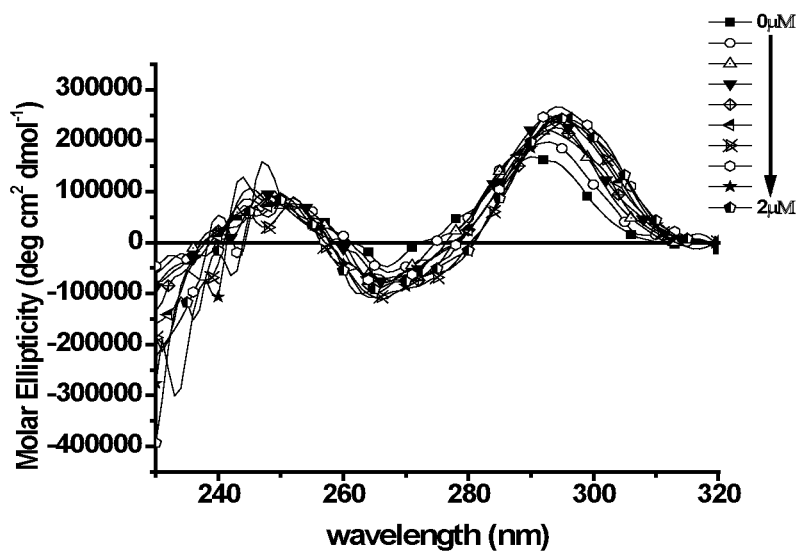

FIG. 5: Depicts changes in the CD signal of TBA (5 μM) upon addition of thrombin in water, in accordance with an implementation of the present disclosure.

Figure 6:
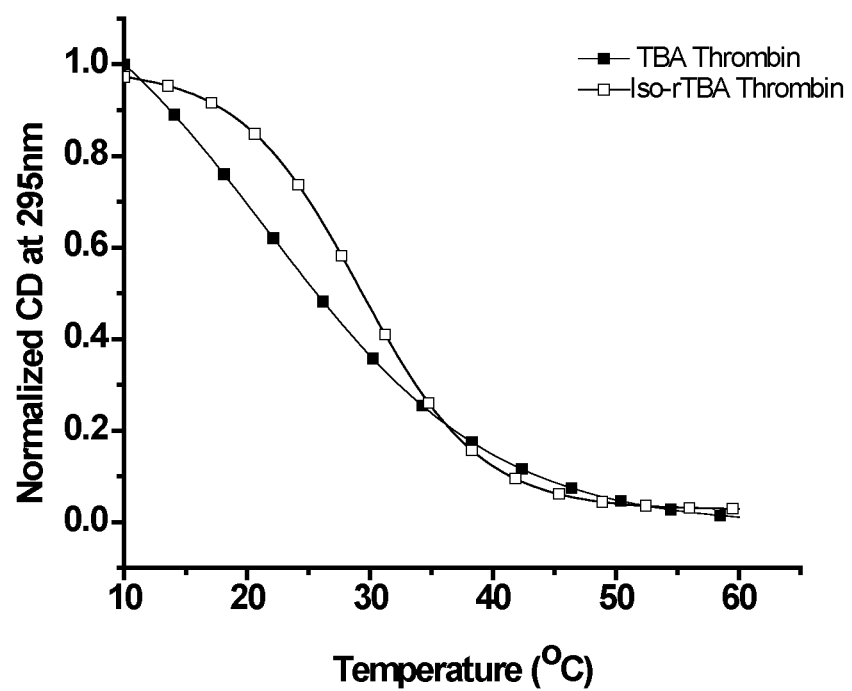

FIG. 6: Depicts CD ($T_m$) of TBA and iso-rTBA after thrombin addition, in accordance with an implementation of the present disclosure.

Figure 7:
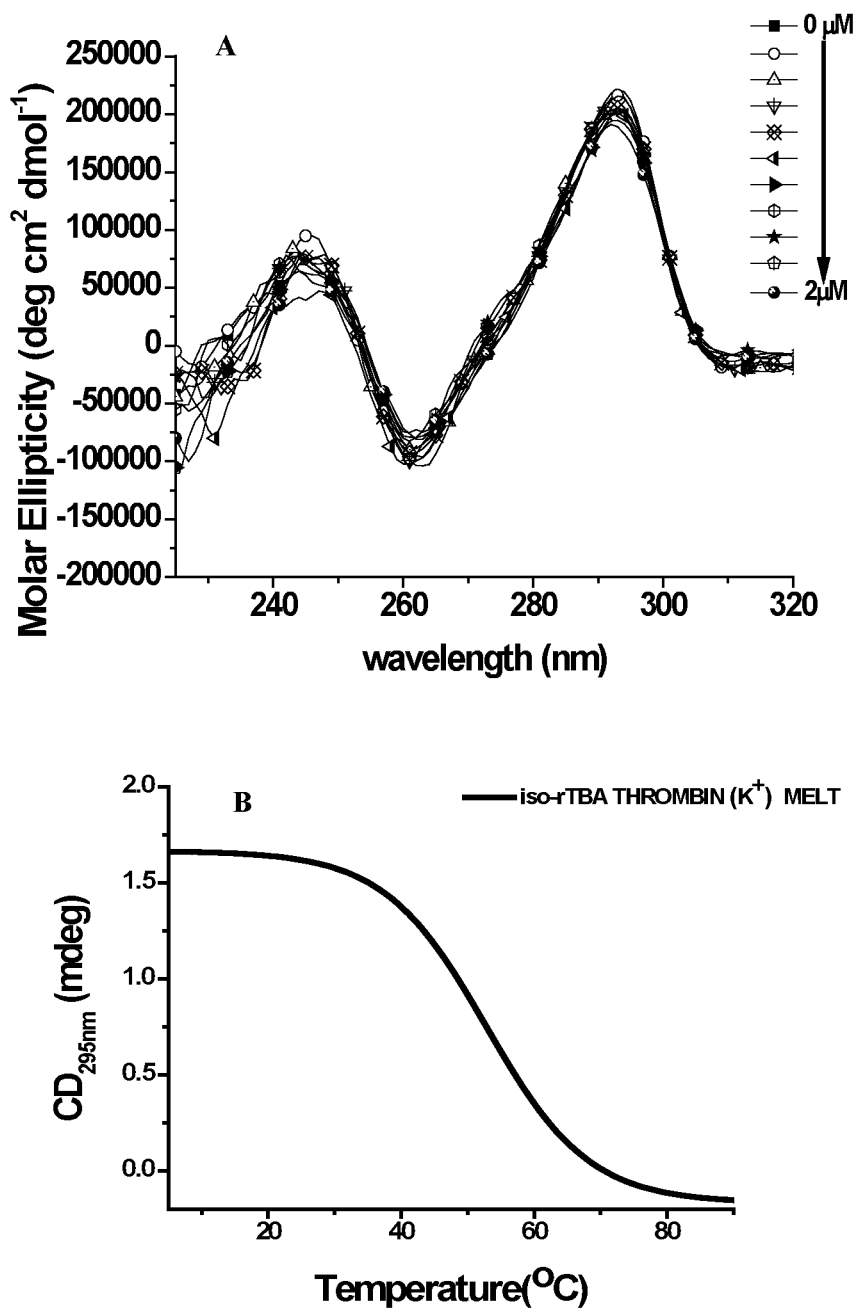

FIG. 7: Depicts (A): Thrombin binding to iso-rTBA in presence of $K^+$ monitored by CD spectra; and (B): CD melting profile of iso-rTBA ($K^+$)-thrombin complex, in accordance with an implementation of the present disclosure.

Figure 8:
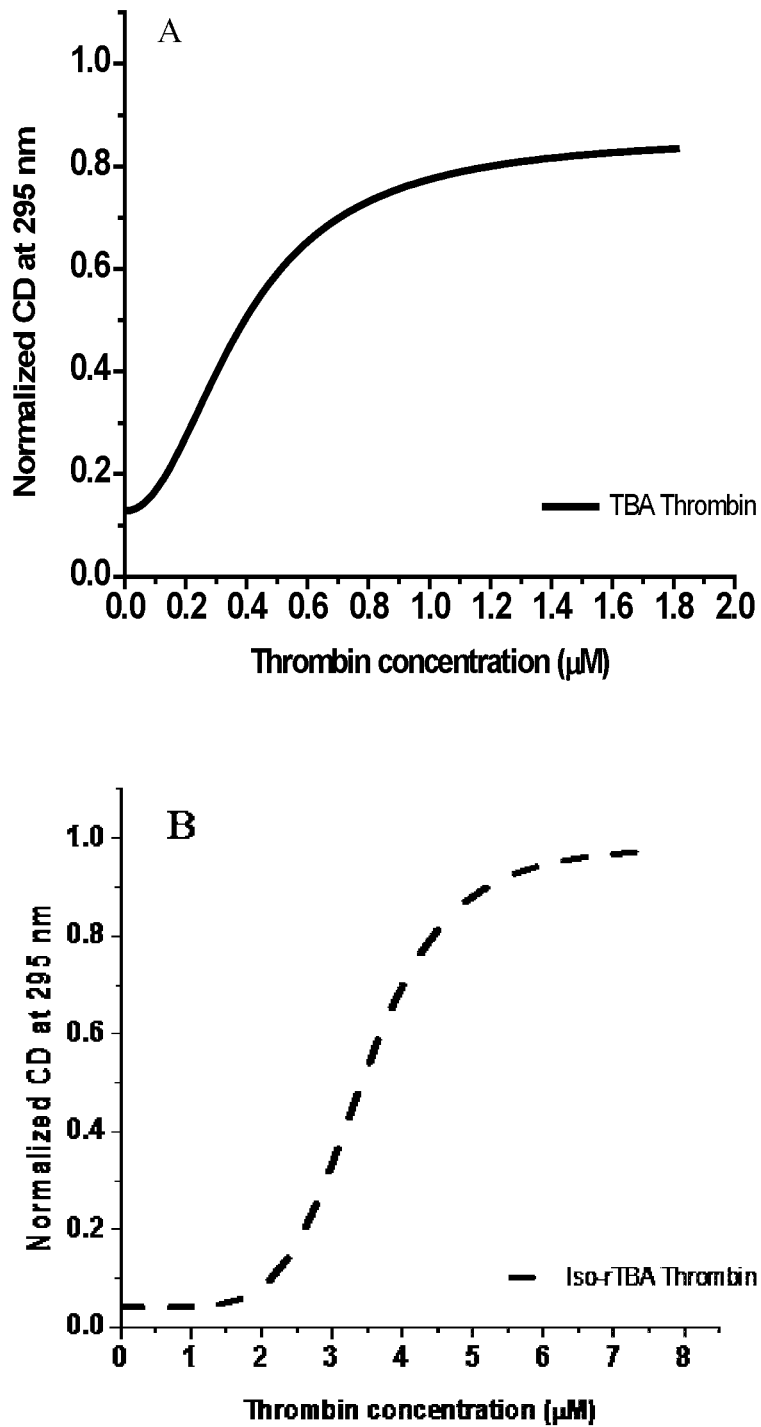

FIG. 8: Depicts CD saturation binding curves for TBA (A) and iso-rTBA (B) with thrombin, in accordance with an implementation of the present disclosure.

Figure 9:
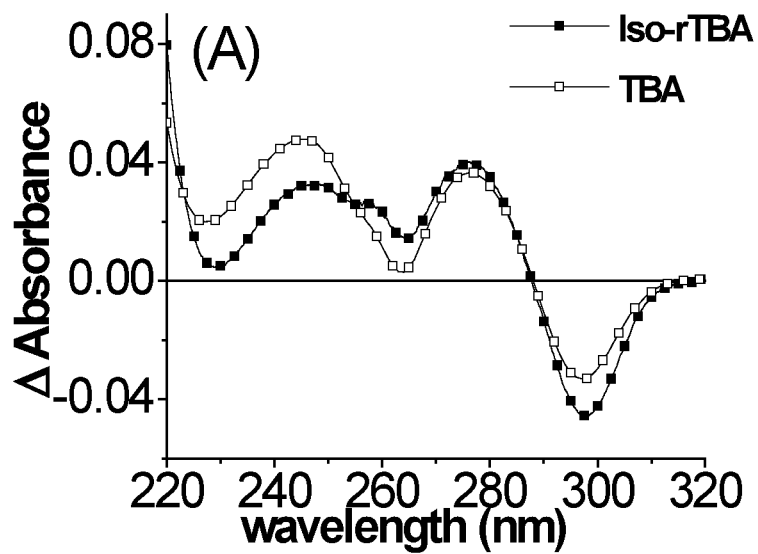
Figure 9:
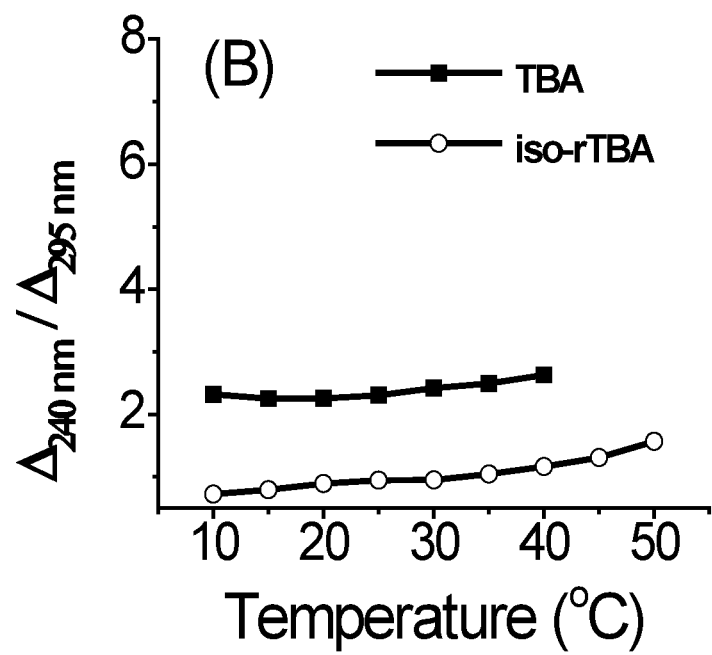

FIG. 9: Depicts (A): UV-TDS of TBA and iso-rTBA taken at 5 μM concentration in 10 mM potassium phosphate buffer, pH 7.2 containing 100 mM KCl. (B): TDS factors for TBA and iso-rTBA taken at 5 μM concentration in 10 mM potassium phosphate buffer, pH 7.2 containing 100 mM KCl, in accordance with an implementation of the present disclosure.

Figure 10:
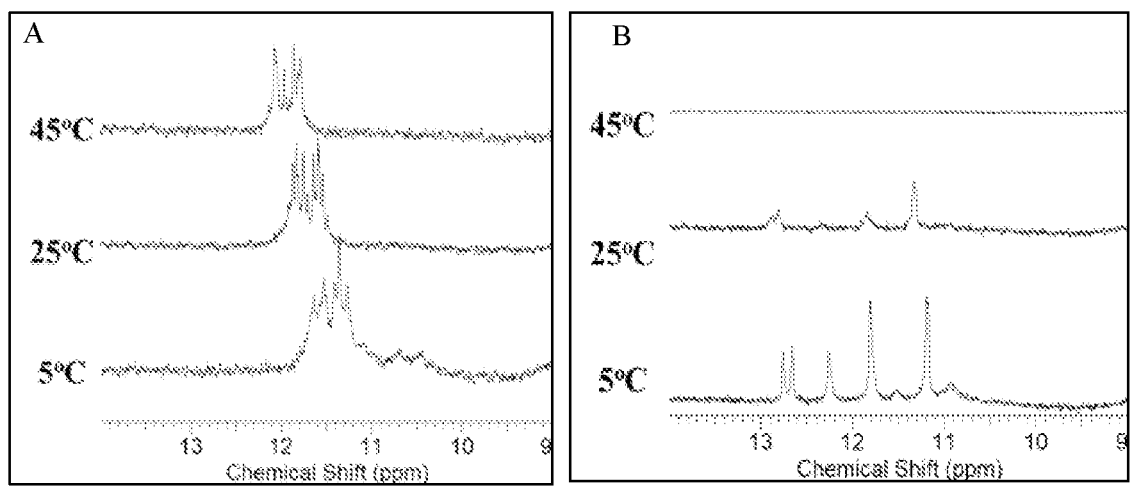

FIG. 10: Depicts imino proton region of the $^1$H NMR spectrum of iso-ITBA (A): in the presence of 100 mM KCl and (B): in the absence of $K^+$ ions. Spectra were recorded at 5° C., 25° C. and 45° C. for a strand concentration of 200 μM in 90:10 v/v $H_2O$: $D_2O$, in accordance with an implementation of the present disclosure.

Figure 11:
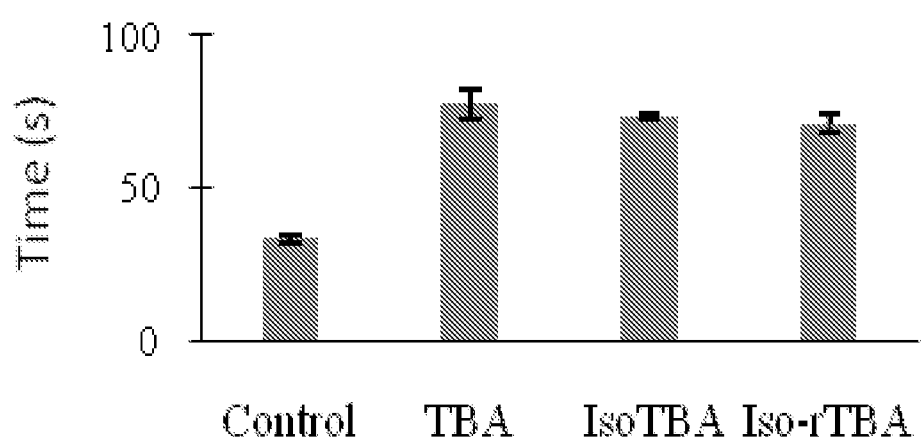

FIG. 11: depicts anti-clotting activity measured by comparing the thrombin-catalyzed fibrin polymerization time, in accordance with an implementation of the present disclosure.

Figure 12:
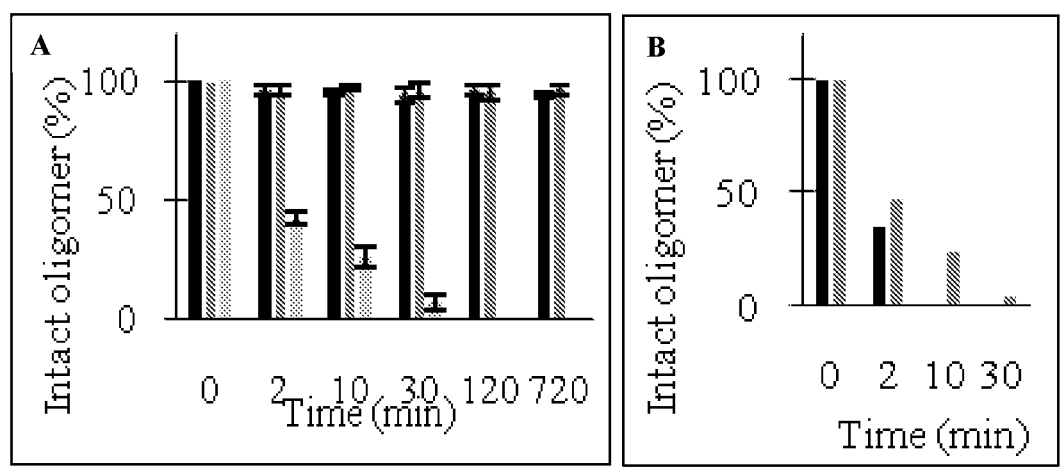

FIG. 12: Depicts stability of oligomers (7.5 μM) at 37° C. to hydrolysis by nucleases. A): RNase A (0.05 U); 50 mM MOPS buffer at pH 7.0, and B): SVPD (0.015 U); 100 mM Tris-HCl (pH 8.5) containing 15 mM $MgCl_2$, 100 mM NaCl. (TBA: black; iso-rTBA: dark gray; random RNA 12mer: light gray), in accordance with an implementation of the present disclosure.

DETAILED DESCRIPTION OF THE INVENTION

While the invention has been disclosed with reference to certain embodiments, it will be understood by those skilled in the art that various changes may be made and equivalents may be substituted without departing from the scope of the invention. In addition, many modifications may be made to adapt to a particular situation or material to the teachings of the invention without departing from its scope.

Throughout the specification and claims, the following terms take the meanings explicitly associated herein unless the context clearly indicates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

The tables, figures and protocols have been represented where appropriate by conventional representations in the drawings, showing only those specific details that are pertinent to understanding the embodiments of the present invention so as not to obscure the disclosure with details that will be readily apparent to those of ordinary skill in the art having benefit of the description herein.

As used herein, the terms "oligomer" and "aptamer" with reference to the thrombin-binding are used interchangeably, when used in the context of the present invention refers to nucleotide or peptide molecules that bind to a specific target molecule. The thrombin binding oligomer or aptamer (TBA) binds and inhibits thrombin, leading to inhibition of clotting.

Accordingly, to accomplish the objectives of the present invention, the inventors disclose stable, guanine-rich 2'-5' linked isoRNA sequences capable of forming thermally stable unimolecular antiparallel G-quadruplexes for efficient binding to thrombin, to ensure a good anticoagulant activity.

In an embodiment of the present invention, the 2'-5' linked isoRNA sequence forms thermally stable unimolecular antiparallel G-quadruplexes.

In another embodiment of the present invention, the 2'-5' linked iso-RNA sequence includes an RNA 2'-O-phosphoramidite.

In still another embodiment of the present invention, 2'-5'-linked isoRNA includes RNA 2'-O-phosphoramidite monomers in comparison to the prohibitively expensive DNA 2'-O-phosphoramidite monomers of 2'-5'-linked isoDNA making its process of preparation cost effective.

In yet another embodiment of the present invention, the 2'-5'-linked isoRNA is an analogous sequence to the known thrombin-binding DNA aptamer (TBA) represented by SEQ ID No. 1.

In another embodiment of the present invention, SEQ ID NO: 1 is:

5'-r(GGUUGGUGUGGUUGG)-2'.

In still another embodiment of the present invention, the 'r' in the SEQ ID NO: 1 represents an RNA sequence and includes isoRNA substitutions represented by 3'-R, wherein R includes but is not limited to OH, OMe, F, Cl, Br, OEt, O-methoxymethyl (OMOM), and O-(2-methoxyethyl) (OMOE).

In the present invention, 2'-5'-linked isoRNA sequences as an alternative backbone for the possible thermally stable G-quadruplex formation is considered for the following reasons:

The 2'-5'-linkages maintain compact backbone geometry due to the anomeric effect on the substituted sugar leading to the S-type geometry sugar conformations.

The S-type sugar geometry in isoRNA allows a favorable equilibrium shift towards the syn guanine conformation required in guanine residues in the antiparallel orientation of strands in the unimolecular folded quadruplex structure.

The S-type of sugar in isoRNA puts the nucleobase in a pseudo-equatorial orientation, which allows both, syn- and anti-orientation about the glycosidic bond, an important feature, making the G-quadruplex amenable to adopting the antiparallel folding topology.

The 2'-5'-linked isoRNA oligomers are relatively stable to exonuclease degradation and also resistant to other nucleases, such as snake venom phosphodiesterase (SVPD).

In an embodiment of the present invention, the 2'-5'-linked isoRNA sequence is highly resistant to RNase and also resistant to other nucleases, such as snake venom phosphodiesterase (SVPD).

In the present invention, 2'-5'-linked isoRNA oligomers are synthesized by β-cyanoethyl phosphoramidite chemistry using solid-phase synthesis. In iso-rTBA, universal columns from Bioautomation, and an extended coupling time of 10 s were used. After post-synthetic cleavage of protecting groups and cleavage from the support, HPLC purification yielded pure oligonucleotides that were characterized by MALDI-TOF analysis.

In an embodiment of the present invention, there is provided a composition comprising the guanine-rich 2'-5'-linked isoRNA sequences with one or more pharmaceutically acceptable excipients.

In another embodiment of the present invention, the guanine rich 2'-5' linked isoRNA sequences may include pharmaceutical composition prepared by methods known in the art. In an optional embodiment of the present invention, the pharmaceutical composition comprising the guanine rich 2'-5' linked isoRNA will be injectible.

In an embodiment of the present invention, the stable, non-genetic, guanine rich 2'-5'-linked isoRNA oligomers capable of forming G-quadruplexes are further characterized by CD spectroscopy, UV-absorbance scans, NMR spectroscopy, anti-clotting measurements and stability study.

In another embodiment of the present invention, the stable antiparallel G-quadruplex formation is observed with iso-rTBA in the presence of $K^+$ ions. FIG. 3 exhibits that when UV-$T_m$ measurements were carried out at a higher strand concentration of 20 μM, no appreciable differences were observed ($\Delta T_m$=+2 to −2° C.), confirming the unimolecularity of the quadruplex.

In still another embodiment of the present invention, the 2"-5'-linked RNA oligomer is thermally stable, exhibiting a melting temperature of $T_m=52°$ C. FIG. 7 depicts that iso-rTBA forms a stable G-quadruplex with thrombin in the presence of K$^+$ ions, with thermal stability similar to that of iso-rTBA alone with K$^+$ ions (absence of thrombin). The $T_m$ comparison table of Table 1 exhibits that, the iso-rTBA quadruplex ($T_m=52°$ C.) is found to be more stable than TBA ($\Delta T_m=+2°$ C.), and isoTBA ($\Delta T_m=+23°$ C.) and forms a very stable antiparallel G-quadruplex in the presence of K$^+$ ions.

In yet another embodiment of the present invention, the iso-rTBA: thrombin complex is also found to be more thermally stable ($T_m=29°$ C.) than the TBA: thrombin complex ($T_m=22°$ C.) indicating the superiority of iso-rTBA.

In still another embodiment of the present invention, the iso-rTBA effects anticoagulation at almost the same level as TBA and isoTBA. FIG. 11 depicts that the anti-clotting effect of iso-rTBA (clotting time 70.9 s) is found to be similar to TBA (clotting time 77.6 s), and isoTBA (clotting time 73.4 s). (Experiments were performed in saline at 37° C. and repeated at least three times independently. The error bars indicated the standard deviation of these measurements. Control represents no added oligomer).

In yet another embodiment of the present invention, the iso-rTBA is resistant to hydrolysis by RNase A. FIG. 12A depicts that the iso-rTBA is extremely stable and remains intact even after prolonged exposure of 12 h by RNAase, behaving similar to TBA, in spite of its RNA-like ribose backbone.

In still another embodiment of the present invention, the iso-rTBA is exposed to hydrolysis by snake venom phosphodiesterase (SVPD). FIG. 12B depicts that the iso-rTBA is more resistant to the SVPD enzyme, with a half-life of 1.9 minutes, whereas, TBA shows lower resistance to the enzyme, with a half-life of 0.8 minutes; 4% intact iso-rTBA is still observed after 30 min, while TBA is completely consumed within 10 min.

EXAMPLES

The following examples are given by way of illustration only and therefore should not be construed to limit the scope of the present invention in any manner.

Example 1:—Oligonucleotide Synthesis

3'-5'-linked TBA and 2'-5'-linked iso-rTBA were synthesized in-house on a Bioautomation Mermade-4 DNA synthesizer employing β-cyanoethyl phosphoramidite chemistry. The 2'-deoxy-3'-phosphoramidites (for TBA) were obtained from ChemGenes and 3'-TBDMS-protected 2'-phosphoramidites (for iso-rTBA), from Glen Research. Universal columns procured from Bioautomation were used for 2'-5'-linked oligomer synthesis. Oligonucleotides were cleaved from the solid support by treating with aqueous ammonia at 60° C. for 6 h and then concentrated. Post-synthesis, deprotection of the TBDMS group was achieved by treatment with triethylamine trihydrofluoride for 2 h, followed by purification.

Example 2:—HPLC Analysis

Oligonucleotides (Iso-rTBA and TBA) were purified by RP-HPLC on a C18 column using Waters system (Waters Delta 600e quaternary solvent delivery system, 2998 photodiode array detector, and Empower2 chromatography software). FIG. 1 shows the HPLC chromatograms of iso-rTBA and TBA.

An increasing gradient of acetonitrile in 0.1 M triethylammonium acetate (pH 7.0) was used. The molecular weight of all oligonucleotides was verified by MALDI-TOF analysis (refer FIG. 2).

Example 3:—CD Studies

CD spectra were recorded on a Jasco J-815 CD spectrometer equipped with a Jasco PTC-424S/15 peltier system. 5 mm path-length quartz cuvettes were used for a sample volume of 2 ml and strand concentration of 5 μM in potassium phosphate buffer (10 mM, pH 7.2) containing 100 mM KCl. Oligomers in buffer were annealed by heating at 95° C. for 5 min, then slowly cooled to room temperature, followed by refrigeration for 3 to 4 h before use. Spectral scans over a range of 320 nm to 200 nm were collected as accumulations of 3 scans at a scanning rate of 100 nm min-1. CD melting was performed by monitoring CD intensity at 295 nm against temperature over the range 5-90° C. at a heating rate of 3° C. per min.

The thrombin-binding ability and affinity were also studied when repetitive amounts of thrombin were added to an aqueous solution of iso-rTBA.

Results: The CD spectrum of 2'-5'-iso-rTBA displayed positive bands at ~295 nm and ~240 nm, and a negative band at ~260 nm in the presence of K$^+$ ions, indicating a characteristic antiparallel G-quadruplex topology, as observed for TBA.

The iso-rTBA quadruplex (Table 1, $T_m=52°$ C.) was also found to be more stable than TBA ($\Delta T_m=+2°$ C.), and isoTBA ($\Delta T_m=+23°$ C.). Thus, iso-rTBA formed a very stable antiparallel G-quadruplex in the presence of K$^+$ ions. (Refer Table 1)

TABLE 1

CD-melting data of oligomers recorded at 295 nm.

| | CD $T_m$ (° C.), K$^+$ | CD $T_m$ (° C.), thrombin |
|---|---|---|
| iso-rTBA | 52 | 29 |
| TBA | 50 | 22 |
| isoTBA | 29 | <10 |
| rTBA | 54[#] | Nd |

[#]indicates that the parameter was measured at 263 nm (Joachimi, A.; Benz, A.; Hartig, J. S. A comparison of DNA and RNA quadruplex structures and stabilities. Bioorg. Med. Chem. 2009, 17, 6811-6815).
nd = not determined.

FIG. 4 indicates the difference in CD spectra of iso-rTBA in the absence and presence of K$^+$ ions. In the presence of K$^+$ ions, the typical signature of an antiparallel G-quadruplex, viz., maximum near 295 nm with minimum near 260 nm were observed, while in the absence of any added cations, a maximum at 255 nm with a minimum at 287 nm were observed.

The drastic changes observed in the CD signal upon addition of thrombin, included a decrease in intensity of the 255 nm maximum and 287 nm minimum, and a concomitant appearance and increase in intensity of a maximum at 295 nm (refer FIG. 6). Thus, the interaction of thrombin with iso-rTBA and its chaperone action inducing an antiparallel topology in iso-rTBA was strongly evident. In comparison, when thrombin was added to TBA, an increase in the maximum near 295 nm was observed, together with a shift towards 300 nm (refer FIG. 5), as reported earlier for this oligomer.

The iso-rTBA: thrombin complex was also found to be more thermally stable ($T_m=29°$ C.) than the TBA: thrombin complex ($T_m=22°$ C., refer Table 1 and FIG. 6), indicating the superiority of iso-rTBA.

When the experiment was performed in the presence of K$^+$ ions, there was negligible change in the CD spectrum of the pre-formed antiparallel iso-rTBA G-quadruplex (refer FIG. 7), as the oligomer was already folded in the antiparallel topology reported for iso-rTBA, in the presence of K$^+$ ions. The thermal stability of the iso-ITBA: K$^+$ complex was largely unchanged upon addition of thrombin, and was similar to that of the iso-rTBA: K$^+$ complex, in the absence of thrombin (refer Table 1).

The K$_d$ for complexes of thrombin with TBA and iso-rTBA were calculated from the CD saturation binding curves (refer FIG. 8) obtained by titrating solutions of the TBA/iso-rTBA oligomers with thrombin.

TABLE 2

Calculation of K$_d$ and n

| Oligomer | K$_d$ | n |
|---|---|---|
| TBA | $3.8 \times 10^{-7}$M | 1 |
| Iso-rTBA | $3.4 \times 10^{-6}$M | 4 |

Calculation of K$_d$ and n

K$_d$ and n were calculated using the formula $$\theta = \frac{[L]}{[L] + K_d}$$

$$\log\left(\frac{\theta}{1-\theta}\right) = n\log[L] - \log[K_d]$$

Where, θ is the normalized CD amplitude at 295 nm, [L] is the ligand (Thrombin) concentration and K$_d$ is the dissociation constant, which is equivalent to 1/K$_a$.

The K$_d$ value for thrombin with iso-rTBA ($3.4 \times 10^{-6}$M) was found to be one order of magnitude higher than for TBA ($3.8 \times 10^{-7}$M). Further, iso-rTBA was found to bind to 4 molecules (n) of thrombin, compared to 1 molecule in the case of TBA, as a 4-fold higher concentration of thrombin was required for the CD signal to reach saturation with iso-rTBA in comparison to TBA.

Example 4:—UV Studies

UV-absorbance scans of the TBA and iso-rTBA oligomers were recorded using 10 mm pathlength quartz cells on an Analytik Jena SPECORD® 200 plus spectrometer equipped with a peltier-controlled temperature controller and at a scanning speed of 5 nm sec-1. The TBA and iso-rTBA oligomers (5 μM strand concentration) were annealed in potassium phosphate buffer (10 mM, pH 7.2), containing 100 mM of the appropriate cations. The oligomer concentration was calculated on the basis of absorbance from molar extinction coefficients of the corresponding nucleobases of DNA. Thermal difference spectra (TDS) were obtained by subtracting the UV-absorbance spectral scan of the sample at temperatures below (i.e., 10° C.) from that above (i.e., 90° C.) the melting temperature (T$_m$). The TDS factor is the absolute value of the ratio of $\Delta A_{240\ nm}/\Delta A_{295\ nm}$, where ΔA is the difference, at a given 2, between the absorbance above (i.e., 90° C.) and at a given temperature, T, below the melting temperature (where T=5° C., 10° C.) etc. up to the melting temperature, T$_m$.

Results:

The UV-TDS plots for TBA and iso-rTBA were similar and are depicted in FIG. 9A. They showed a minimum at ~295 nm, and maxima at ~243 nm and ~273 nm, typically signifying the presence of a G-quadruplex in both the cases. The TDS factors for TBA and iso-rTBA in the presence of K$^+$ ions were plotted as absolute values of $\Delta A_{240\ nm}/\Delta A_{295\ nm}$ and are depicted in FIG. 9B. For TBA and iso-rTBA, the TDS factor obtained was ~2 or <2 respectively, undoubtedly signifying antiparallel G-quadruplexes.

Stable antiparallel G-quadruplex formation was observed with iso-rTBA in the presence of K$^+$ ions. Negligible hysteresis ($\Delta T_m \leq 2°$ C., Table 3 and FIG. 3) was observed, indicative of a unimolecular complex for TBA and iso-rTBA. Further, when the UV-T$_m$ measurements were carried out at a higher strand concentration of 20 UM (refer FIG. 3), no appreciable differences were observed ($\Delta T_m = +2$ to $-2°$ C.), confirming the unimolecularity of the quadruplex. The data is listed in Table 3.

TABLE 3

Table 3. UV- T$_m$ data for TBA and iso-rTBA

| | TBA (K$^+$) | | | | Iso-rTBA (K$^+$) | | | |
|---|---|---|---|---|---|---|---|---|
| Strand conc (μM) | T$_m$ (heat) ° C. | T$_m$ (cool) ° C. | ΔT$_m$ (20 μM – 5 μM) ° C. | ΔT$_m$ (heat – cool) ° C. | T$_m$ (heat) ° C. | T$_m$ (cool) ° C. | ΔT$_m$ (20 μM – 5 μM) ° C. | ΔT$_m$ (heat – cool) ° C. |
| 5 | 51 | 50 | +2 | +1 | 49 | 51 | −1 | −2 |
| 20 | 49 | — | — | — | 48 | 50 | — | −2 |

Example 5:—NMR Experiments $^1$H NMR spectra were acquired on a Bruker Avance IIIHD700 NMR spectrometer operating at 700.13 MHz for 1H using a 5 mm TXI probe. The spectral window was set to 20 ppm with the carrier positioned on the water signal. Suppression of water signal was achieved by using a standard Bruker pulse sequence incorporating excitation sculpting with selective RF pulses and gradients. Spectra were recorded with a relaxation delay of 4s and 4096 scans. The raw data were processed with a Gaussian function for the improvement of the signal-to-noise ratio. The temperature during the measurements was controlled using a Bruker BVT 3000 unit. HPLC-purified iso-rTBA was taken at 200 μM concentrations in 90:10 v/v H$_2$O: D$_2$O with or without 100 mM KCl in 3 mm NMR tubes for recording spectra.

Results:

As observed for TBA and isoTBA, comparable imino proton chemical shifts were observed for iso-rTBA as well (refer FIG. 10), indicative of a hydrogen-bonded G-quadruplex. Unlike isoTBA, where the 1H NMR spectrum did not show any imino proton resonances in this region in the absence of added cations, some signals were observed for iso-rTBA in this region (FIG. 10B), although these were scattered compared to those observed in the presence of K$^+$ ions (FIG. 10A). In the absence of K$^+$ ions, very weak and broad signals were observed, extending to ~13.0 ppm indicating the presence of either the Watson-Crick type base pairs or other non-canonical, random aggregates.

Temperature-dependent changes in the 1H NMR spectrum were recorded, which showed that in the absence of K$^+$ ions, the imino signals disappear at higher temperature (45° C.) indicating disruption of hydrogen-bonded structures. In the presence of K$^+$ ions, two sets of imino signals were present at low temperatures, one being very weak and broad relative to the other. This is indicative of multiple G-quadruplex conformations or simple aggregation of G-rich strands at high concentrations. At 25° C., the weaker signals disappeared and a single set of narrow imino peaks equal to the number of guanines in the sequence were observed indicating a single dominant quadruplex conformation.

Example 6:—Anticlotting Measurements

Clotting time experiments were performed at 37° C. on a Start-Max (Stago) coagulation analyzer. Each experiment was repeated at least thrice; the standard deviation was +1 s. Each commercial reagent was reconstituted according to the manufacturer's protocol. Bovine thrombin (Tulip Diagnostics, 0.1 NIH units) was incubated with TBA or iso-rTBA, as applicable, at 0.25 µM oligomer concentration for 1.5 min before addition to fibrinogen from human plasma (Aldrich, 3.5 µM). The clotting time(s) was measured as the time taken from the addition of thrombin till the polymerization of fibrin.
Results:
FIG. 11 showed the anticlotting activity measured by comparing the thrombin-catalyzed fibrin polymerization time. The anti-clotting effect of iso-rTBA (clotting time 70.9 s) was found to be similar to TBA (clotting time 77.6 s), and isoTBA (clotting time 73.4 s). Thus, not only was the RNA backbone of iso-rTBA able to fold into an antiparallel quadruplex but, noteworthily, it was also able to affect anticoagulation to almost the same level as TBA and isoTBA.

Example 7:—Stability Study

Stability of Oligonucleotides to RNase A
The reactions were performed in 1.5 ml plastic tubes with a screw cap immersed in a water bath at 37° C. Incubation was carried out in 50 mM MOPS buffer at pH 7.0. The samples were prepared by adding the oligonucleotides (iso-rTBA, ITBA, random RNA, or TBA at 7.5 µM concentration) to a solution of the RNase enzyme (0.05 U) in MOPS buffer. Aliquots were collected at specific times after initiation of the reaction, the enzyme was inactivated by heating at 90° C. for 3 min, and samples were analyzed by HPLC to determine the quantity of oligonucleotide remaining intact at each time point.
Results: TBA, being a DNA oligomer, was resistant to hydrolysis by RNase A that is an RNA-hydrolyzing enzyme. On the other hand, the random sequence RNA 12mer was rapidly hydrolyzed, and displayed a half-life of 1.5 min. The iso-rTBA was extremely stable and remained intact even after prolonged exposure of 12 h, behaving similar to TBA, in spite of its RNA-like ribose backbone (refer FIG. 12A).
SVPD Stability Study
TBA and iso-rTBA (7.5 µM) stability to hydrolysis by snake venom phosphodiesterase (SVPD) was studied at 37° C. in 100 mM Tris-HCl buffer (pH 8.5) containing 15 mM MgCl$_2$, 100 mM NaCl, and SVPD (0.015U). Aliquots were removed at successive time intervals, heated at 90° C. for 3 min to inactivate the nuclease, and analyzed by RP-HPLC to measure the percentage of oligonucleotides remaining intact.
Results:
Both TBA and iso-rTBA were hydrolyzed by SVPD. The iso-rTBA was more resistant to the enzyme, with a half-life of 1.9 minutes. TBA showed resistance to the enzyme, with a half-life of 0.8 minutes; 4% intact iso-rTBA was still observed after 30 min, while TBA was completely consumed within 10 min (refer FIG. 12B).

Advantages of the Invention

Thermally stable unimolecular antiparallel iso-rTBA G-quadruplex disclosed in the present disclosure is capable of binding to thrombin and inhibiting clotting. Iso-rTBA is highly resistant to RNase A and nucleases such as snake venom phosphodiesterase (SVPD). The process of preparing iso-rTBA disclosed in the present disclosure is cost-effective.

We claim:
1. G-quadruplex forming iso-RNA oligomers comprising a 2'-5'-linked iso-RNA sequence; wherein the G-quadruplex forming iso-RNA oligomers are configured to bind thrombin, wherein the 2'-5'-linked isoRNA sequence is a thrombin-binding aptamer (iso-rTBA) comprising SEQ ID NO:1.
2. The iso-RNA oligomers as claimed in claim 1, wherein the 2'-5'-linked iso-RNA sequence forms unimolecular antiparallel G-quadruplexes.
3. The iso-RNA oligomers as claimed in claim 1, wherein the 2'-5'-linked iso-RNA sequence was made using an RNA 2'-O-phosphoramidite.
4. The iso-RNA oligomers as claimed in claim 1, wherein the SEQ ID NO: 1 is 5'-r(GGUUGGUGUGGUUGG)-2', wherein "r" is an RNA oligomer and includes 3'-R substitutions, wherein 'R' is selected from OH, OMe, F, Cl, Br, OEt, OMOM, and OMOE.

5. The iso-RNA oligomers as claimed in claim 1, wherein the oligomers exhibit complete resistance towards RNase A and partial resistance towards snake venom phosphodiesterase (SVPD).

6. The iso-RNA oligomers as claimed in claim 1, wherein the 2'-5'-linked RNA oligomers have a melting temperature ($T_m$) of 52° C.

7. The iso-RNA oligomers as claimed in claim 1, having a melting temperature ($T_m$) of 29° C. when bound to thrombin.

8. A composition comprising the G-quadruplex forming iso-RNA oligomers of claim 1 along with at least one pharmaceutically acceptable excipient.

* * * * *